(12) United States Patent
Horstmann et al.

(10) Patent No.: US 6,277,400 B1
(45) Date of Patent: Aug. 21, 2001

(54) EXTENDIBLE TRANSDERMAL THERAPEUTIC SYSTEM

(75) Inventors: Michael Horstmann; Walter Müller, both of Neuwied; Wolfgang Laux, Diez, all of (DE)

(73) Assignee: LTS Lohmann Therapie-Systeme AG (DE)

(*) Notice: Subject to any disclaimer, the term of this patent is extended or adjusted under 35 U.S.C. 154(b) by 0 days.

(21) Appl. No.: 09/367,341

(22) PCT Filed: Jan. 30, 1998

(86) PCT No.: PCT/EP98/00496

§ 371 Date: Oct. 1, 1999

§ 102(e) Date: Oct. 1, 1999

(87) PCT Pub. No.: WO98/34600

PCT Pub. Date: Aug. 13, 1998

(30) Foreign Application Priority Data

Feb. 11, 1997 (DE) ............................................. 197 05 138

(51) Int. Cl.[7] ............................ A61F 13/02; A61F 13/00; A61L 15/16
(52) U.S. Cl. ............................ 424/448; 424/449; 424/443
(58) Field of Search ........................... 424/449, 448, 424/447

(56) References Cited

U.S. PATENT DOCUMENTS

5,240,711 * 8/1993 Hille et al. ............................ 424/448

FOREIGN PATENT DOCUMENTS

| 0 196 769 | * 10/1986 | (EP) . |
| WO 89/05663 | * 6/1989 | (EP) . |
| WO 89 05663 | 6/1989 | (EP) . |
| 0 366 240 | 5/1990 | (EP) . |
| 0 379 044 | * 7/1990 | (EP) . |
| 0 430 019 | 6/1991 | (EP) . |
| 0 483 370 | * 5/1992 | (EP) . |
| 59-039827 | 3/1984 | (JP) . |

* cited by examiner

Primary Examiner—Thurman K. Page
Assistant Examiner—Isis Ghali
(74) Attorney, Agent, or Firm—D. Peter Hochberg; Katherine R. Vieyra; William H. Holt

(57) ABSTRACT

An active ingredient-containing transdermal therapeutic system with a nonadhesive backing layer, with an active ingredient-containing reservoir layer and with a self-adhesive surface facing the skin, where appropriate with redetachable protecting layer, is characterized by an elastic or plastically extensible diffusible backing layer with a metal layer which acts as permeability barrier for auxiliaries and active ingredients in the reservoir layer and is formed by film growth, in particular a metallization layer.

5 Claims, 1 Drawing Sheet

EXTENDIBLE TRANSDERMAL THERAPEUTIC SYSTEM

Figure 1:
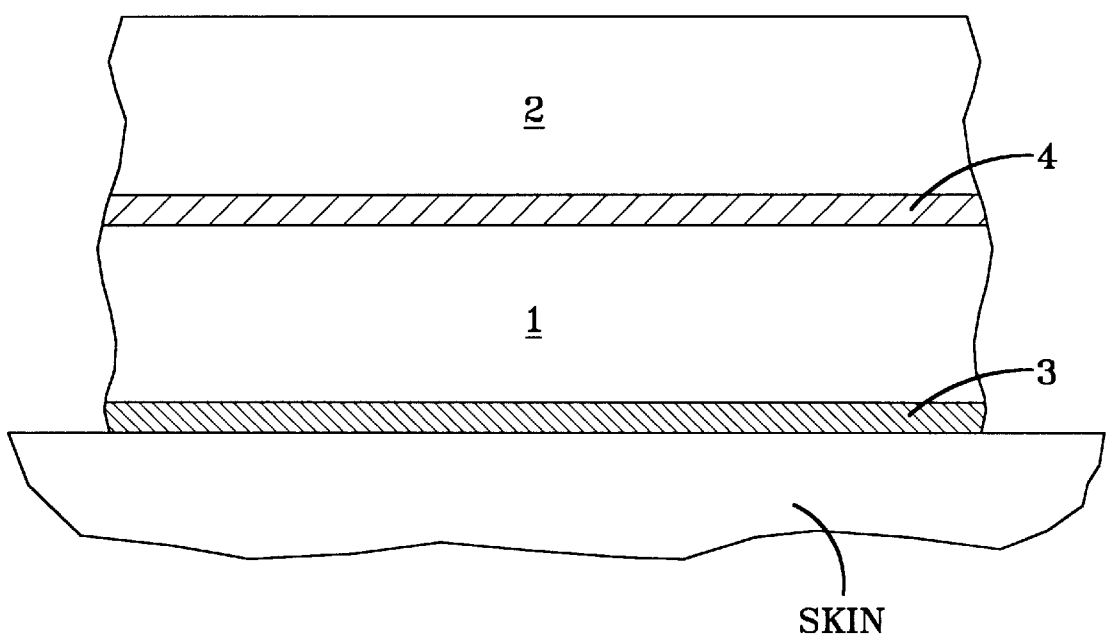

The invention relates to an active ingredient-containing transdermal therapeutic system with a nonadhesive backing layer, with an active ingredient-containing reservoir layer and with a self-adhesive surface facing the skin, where appropriate with redetachable protecting layer.

It has been known ever since the Middle Ages that pharmaceutical active ingredients can migrate through the human skin and thus medicinal effects can be achieved by preparations of pharmaceutical active ingredients being placed or spread on the skin. These effects are not confined to the skin and the underlying tissue but may, with appropriately suitable substances, extend to remote organs because the active ingredients are, after absorption, distributed by the blood circulation. Transdermal therapeutic systems (TTS) which define not only the active ingredient concentration used but also the application area exactly have in the past become established as novel pharmaceutical administration forms because they provide the required properties in a particularly user-friendly manner.

The possible TTS embodiments have some basic features in common:

1. To prevent unwanted release of active ingredient or else moisture from the skin through the transdermal therapeutic system to the outside, also to prevent adhesion to textiles, an essentially impermeable, nonadhesive backing layer is used.

2. Since transdermal therapeutic systems are intended to adhere to the skin, the layer facing the skin, and occasionally only part of the contour, is made self-adhesive.

3. Because of the self-adhesive properties, a redetachable protecting layer is applied for storage before use.

The backing layer usually consists of pharmaceutically customary materials such as plastic sheets; but paper, nonwovens, textiles and metal foils are also mentioned.

TTS of these types are, despite the advances made, nevertheless also associated with some disadvantages. Thus, the active ingredient-impermeable backing layer with a stable area restricts the comfort of wearing for the patient, the "stiffness" or lack of extensibility of the sheets used in practice results in a limitation to areas with a size of 40 cm². However, since the area-related transport rate through the skin is very low for most pharmaceutical active ingredients, a larger area for the system would be very desirable in order to be able to offer marketable TTS also for such active ingredients.

There have already been attempts to improve the comfort of wearing by using elastic materials for the backing layer (for example U.S. Pat. No. 5,246,705) but in this case express attention was paid to the impermeability of the material for the advised drug.

It is unfortunate in principle that all elastic and plastically extensible polymeric raw materials suitable for the TTS backing layer are diffusible for most TTS active ingredients, so that transdermal therapeutic systems produced therewith generally display the problem of potential losses of active ingredient (evaporation through the outer surface of the backing layer), especially when very volatile active ingredients are employed.

It is an object of the invention to provide a transdermal therapeutic system with an elastic or plastically extensible backing layer which displays improved stabilization, by comparison with the prior art, against evaporation of the active ingredient present.

This object is achieved according to the invention with a TTS of the type mentioned at the outset, which is characterized by an elastic or plastically extensible diffusible backing layer with a metal layer which acts as permeability barrier for auxiliaries and active ingredients in the reservoir layer and is formed by film growth, in particular a layer resulting from metal vapour deposition. Further particular features are evident from the dependent claims and the description.

FIG. 1 provides a cross sectional side view of an active ingredient-containing transdermal therapeutic system with an active ingredient-containing reservoir layer 1 with a self-adhesive surface 3 facing the skin and a nonadhesive extensible backing layer 2 with a thin vapor deposited metal layer 4 of a thickness of 50–1500 Å.

The elastic, and therefore active ingredient-permeable, backing layer comprises according to the invention a metal layer formed by film growth (sputtering, deposition etc.), in particular a zone of vacuum-coated metal, which is sufficient as barrier for auxiliaries and active ingredients without compromising the desired extensibility of the backing layer.

These properties are achieved in particular with thicknesses of the metal layer in the range from 50 to 1500 Å, in particular from 100 to 300 Å. A certain part is played in this, of course, by the required size of the area of the TTS. Vacuum-coated aluminium layers are particularly preferred, the production of these being generally well known per se.

Also known in the TTS sector is deposition of very thin (8 Å) Al layers onto a 25 μm LDPE film which is intended to serve as substrate or backing layer for a drug-containing adhesive layer with plant extract active ingredients (JP 53 10560 A). However, such a very thin deposit would be inadequate for the effect desired according to the invention.

Furthermore, WO 91-11752 describes an estradiol TTS for whose backing layer a large number of materials is indicated, which also comprises flexible synthetic films with Al metallization. However, this teaching by no means leads to the recognition that inclusion of a metal layer which acts as barrier for losses of active ingredients as very volatile substances and allows the backing layer to be extensible in the surface, in particular an Al layer, in an elastic backing layer makes it possible to achieve particularly suitable transdermal therapeutic systems.

It is in fact surprisingly possible according to the invention to combine the advantageous property of greater pliabilities of the transdermal therapeutic system in the surface with sufficient stability even with problematic active ingredients, because the metal layer not only prevents losses through evaporation, but at the same time provides protection against the harmful effects of light on photosensitive active ingredients and components.

Protection from the effects of light is possible with conventional transdermal systems having an active ingredient-impermeable elongation-stiff backing layer by applying to the outside a pigment-containing coating which is not transparent to light. However, this process cannot be employed for elastic sheets because the mechanically rigid coating systems flake off or at least develop cracks on elongation.

The metallization, in particular aluminization, according to the invention of the backing layer does not comprise a continuous, uniform, sheet-like metal assemblage; on the contrary, submicroscopic crystallites are inserted into the surface and greatly restrict the incidence of light and diffusion, but also permit adequate pliability of the material in the surface.

Hence the invention appears also to be useful for a TTS which has been described in the interim and in which the backing layer is diffusible and contains at least one third of the amount of active ingredient present in the preparation. In these systems (German Patent Application P 195 46 024.3), the backing layer assumes a double function as part of the pharmaceutical reservoir and simultaneously as element of the mechanical strength, and for preventing adhesion outside.

On implementation in practice, the aluminization is advantageously applied to the side of the backing layer facing the skin in order to avoid attrition through surface abrasion on the TTS. Since, especially in the case of the effects of light, the amounts of active ingredient present in the outermost surface of the backing layer are exposed to decomposition by light, it may furthermore be worthwhile to limit the backing layer to an extremely thin polymer layer and to include between the actual backing layer, which is now very thin, and the remaining elements of the transdermal therapeutic system another zone which improves the tensile strength (supporting layer).

The invention can in principle be used with all pharmaceutical active ingredients which pass through the skin. It is, of course, particularly advantageous to use it for volatile active ingredients and auxiliaries. Examples of such substances are nicotine or nitroglycerin as examples of pharmaceutical active ingredients. Ethanol, propanediol and other low molecular weight alcohols, menthol, eucalyptol, limonene and many other terpenes, low molecular weight fatty acids such as, for example, capric acid, dimethyl sulphoxide may be mentioned as examples of typical additives in such preparations, which could migrate to a greater or lesser extent out of the preparation through the backing layer.

Particular advantages furthermore emerge on use of photosensitive substances which occur with numerous organic chemical groups of active ingredients such as, for example, phenothiazines, certain peptides, dihydropyridines (for example nifedipine), opioids and many other groups of active ingredients.

Apart from the active ingredient-permeable backing layer, which contains the active ingredient and which contains the metallized protecting layer, and from a supporting layer which is present where appropriate, the other construction of the transdermal therapeutic system is not critical for achieving the purpose according to the invention. It is therefore possible to employ transdermal systems of every type of construction, whether mono- or multilayer matrix systems, constructions with incorporated active ingredient-containing fibrous preparations, genuine reservoir systems with liquid active ingredient-containing reservoir or systems of other types of construction.

Several materials which are acceptable in particular for pharmaceutical products are suitable in principle for the backing layer: polyvinyl alcohol, styrene/diene block copolymers, polyurethanes, polyvinyl chloride, polymethacrylates, to mention only a few examples.

It may be perfectly worthwhile, for protection and for easier application of the transdermal therapeutic system to the skin, to incorporate an additional supporting layer which is adhesive, has an incorporated abhesive and can be removed again after application of the system.

The invention is explained below by examples:

EXAMPLE 1

A) 10 g of styrene/isoprene/styrene copolymer (Cariflex® TR 1107) are dissolved completely in 20 g of petroleum ether with a boiling range between 80 and 100° C.

The composition is coated in a thickness of about 250 $\mu$m onto a polyester sheet with incorporated abhesive in such a way that, after drying at 35° C. for 4 hours, a uniform layer with a weight per unit area of 50 g/m$^2$ is produced.

After further drying at 80° C. for 20 minutes, an 80 mg/m$^2$ aluminium layer is applied in vacuo.

B) In a separate step, a solution of 20 g of hydrogenated rosin glycerol ester resin (Staybelite Ester® 5 E) and 7 g of styrene/isoprene/styrene copolymer (Cariflex®TR 1107) and 1 g of low viscosity paraffin in 20 g of ethyl acetate is prepared, and 0.5 g of nifedipine is introduced and dissolved completely at room temperature. The composition is coated in a thickness of about 150 $\mu$m onto a polyester sheet with incorporated abhesive in such a way that, after drying at 35° C. for half an hour and subsequent drying at 60° C. for 15 minutes, a uniform layer with a weight per unit area of 35 g/m$^2$ is produced.

The layers of Phase A and Phase B produced in this way are laminated together and spontaneously adhere to give a composite which cannot be loosened manually. The polyester sheet with incorporated abhesive from Phase B and the adhesive layer, and the backing layer are cut out with a contour corresponding to the geometric shape of the preparation in a manner known to the skilled person, and the residues on the outside are removed.

The pharmaceutical form is packed singly in sealable bags. The user removes the medicinal product from the packaging, detaches the protecting layer (release liner) for the adhesive layer, sticks the pharmaceutical form onto a suitable place on the skin and finally detaches the supporting layer (polyester sheet with incorporated abhesive).

What is claimed is:

1. An active ingredient-containing transdermal therapeutic system comprising an active ingredient-containing reservoir layer with a self-adhesive surface facing the skin; and a nonadhesive extensible backing having a metal layer having submicroscopic crystallites inserted into the surface resulting from metal vapor deposition which is formed by film growth and is of a thickness of 50–1500 Å which acts as a permeability barrier for auxiliaries and active ingredients in the reservoir layer, wherein said metal layer is arranged on the skin facing side of the backing layer.

2. The system of claim 1 wherein the thickness of the metal layer is 100–300 Å.

3. The system of claim 1 wherein the metal layer comprises aluminum.

4. The system of claim 1 having a total thickness of 50–250 $\mu$m.

5. The system of claim 1 wherein the backing layer is provided with a supporting layer on the side facing the skin.

* * * * *